United States Patent
Rolain et al.

(10) Patent No.: US 10,837,044 B2
(45) Date of Patent: Nov. 17, 2020

(54) AUTOMATED METHOD FOR ANALYZING AND INTERPRETING AN ANTIMICROBIAL SUSCEPTIBILITY

(71) Applicants: FONDATION MEDITERRANEE INFECTION, Marseilles (FR); UNIVERSITE D'AIX MARSEILLE, Marseilles (FR); ASSISTANCE PUBLIQUE—HOPITAUX DE MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

(72) Inventors: Jean-Marc Rolain, Marseilles (FR); Didier Raoult, Marseilles (FR); Stéphanie Le Page, Aubagne (FR); Sylvain Buffet, Marseilles (FR)

(73) Assignees: FONDATION MEDITERRANEE INFECTION, Marseilles (FR); UNIVERSITE D'AIX MARSEILLE, Marseilles (FR); ASSISTANCE PUBLIQUE—HOPITAUX DE MARSEILLE, Marseilles (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 763 days.

(21) Appl. No.: 15/516,094

(22) PCT Filed: Oct. 5, 2015

(86) PCT No.: PCT/FR2015/052667
§ 371 (c)(1),
(2) Date: Mar. 31, 2017

(87) PCT Pub. No.: WO2016/055724
PCT Pub. Date: Apr. 14, 2016

(65) Prior Publication Data
US 2017/0298408 A1 Oct. 19, 2017

(30) Foreign Application Priority Data
Oct. 6, 2014 (FR) .................................... 14 59559

(51) Int. Cl.
*C12Q 1/20* (2006.01)
*G06T 7/00* (2017.01)
*C12Q 1/04* (2006.01)
*C12Q 1/18* (2006.01)

(52) U.S. Cl.
CPC ............... *C12Q 1/20* (2013.01); *C12Q 1/04* (2013.01); *C12Q 1/18* (2013.01); *G06T 7/0014* (2013.01); *G06T 2207/30024* (2013.01)

(58) Field of Classification Search
None
See application file for complete search history.

(56) References Cited

PUBLICATIONS

Mullett, Charles J., et al. "Computerized antimicrobial decision support: an offline evaluation of a database-driven empiric antimicrobial guidance program in hospitalized patients with a bloodstream infection." International journal of medical informatics 73.5 (2004): 455-460.*

Deshpande, Lalitagauri M., Thomas R. Fritsche, and Ronald N. Jones. "Molecular epidemiology of selected multidrug-resistant bacteria: a global report from the SENTRY Antimicrobial Surveillance Program." Diagnostic microbiology and infectious disease 49.4 (2004): 231-236.*

Non-English International Search Report dated Jan. 29, 2016 for Application No. PCT/FR2015/052667 with English translation.

Korgenski, E. K., et al., "Evaluation of the BIOMIC Video Reader System for Determining Interpretive Categories of Isolates on the Basis of Disk Diffusion Susceptibility Results", Journal of Clinical Microbiology, vol. 36, No. 1, Jan. 1998, pp. 302-304.

Medeiros, A. A., et al., "Evaluation of the Sirscan Automated Zone Reader in a Clinical Microbiology Laboratory", Journal of Clinical Microbiology, vol. 38, No. 4, Apr. 2000, pp. 1688-1693.

Kolbert, M., et al., "Evaluation of the OSIRIS video reader as an automated measurement system for the agar disk diffusion technique", Clinical Microbiology and Infection, vol. 10, No. 5, May 2004, pp. 416-420.

Bert, F., et al., "Evaluation and Updating of the Osiris Expert System for Identification of *Escherichia coli* β-Lactam Resistance Phenotypes", Journal of Clinical Microbiology, vol. 43, No. 4, Apr. 2005, pp. 1846-1850.

Lestari, E. S., et al., "Comparison of the accuracy of disk diffusion zone diameters obtained by manual zone measurements to that by automated zone measurements to determine antimicrobial susceptibility", Journal of Microbiological Methods, vol. 75, No. 2, Oct. 2008, pp. 177-181.

(Continued)

*Primary Examiner* — G Steven Vanni
(74) *Attorney, Agent, or Firm* — Ladas & Parry, LLP; Malcolm J. MacDonald

(57) ABSTRACT

The present invention relates to a method of interpreting different antibiogram images in which it is possible to recognize a phenotype of bacterial resistance relative to antibiotics by comparing photographs using a photographic image bank of the reference antibiogram without any need to interpret them using the EUCAST or CA-SFM interpretation data; providing that for a given phenotype, there is available a collection of photographs of a plurality of bacteria of the same species and of the same phenotype.

21 Claims, 4 Drawing Sheets

(56) References Cited

PUBLICATIONS

Le Page, S., et al. "Real-time video imaging as a new and rapid tool for antibiotic susceptibility testing by the disc diffusion method: A paradigm for evaluating resistance to imipenem and identifying extended-spectrum β-lactamases", International Journal of Antimicrobial Agents, vol. 45, No. 1, Oct. 2015, pp. 61-65.

* cited by examiner

AUTOMATED METHOD FOR ANALYZING AND INTERPRETING AN ANTIMICROBIAL SUSCEPTIBILITY

The present invention relates to a method serving to automate reading and interpreting tests of the sensitivity of microorganisms to antimicrobial agents, in the field of chemical microbiology.

This invention may be applied mainly in bacteriology to tests of the sensitivity of bacteria to antibiotics, which tests are referred to as "antiobiograms", and also in other fields in the study of infectious diseases, such as micrological tests of the sensitivity of fungi to antifungal agents, which tests may be referred to as antifungigrams.

In the present description, the term "antibiogram" is used as a general term both for testing bacteria against antibiotic compounds and for testing fungi against antifungal compounds.

An antibiogram is a laboratory technique seeking to test the sensitivity of a strain of bacteria to one or more potential or known antibiotics by evaluating the extent to which growth of the bacterium is inhibited. The principle consists in placing a culture of bacteria in the presence of one or more antibiotics and in observing the consequences on the development and the survival of the culture. To do this, it is possible by way of example to place a plurality of antibiotic-impregnated wafers on a bacterial strain deposited on a solid culture medium. The antibiotic then diffuses from the wafer, thereby creating a concentration gradient around the wafer with a zone of growth inhibition that is visible to the naked eye in the form of a dark ring around the wafer if the bacterium is sensitive to the antibiotic. There are three types of interpretation depending on the diameter of the circle constituting the inhibition zone surrounding the disk of the antibiotic wafer: the strain or bacterium may be sensitive, intermediate, or resistant.

Such wafers and their varying doses of antibiotic are standardized in compliance with the recommendations of the expert systems of the European Committee on Antimicrobial Susceptibility Testing (EUCAST): www.eucast.org, [T. Winstanley, P. Courvalin (2011), "Expert systems in clinical microbiology" Clin. Microbiol. Rev. 24: pp. 515-556. 24/3/515 [pli]; 10.1128/CMR.00061-101, and R. Leclercq, R. Canton, D. F. Brown, C. G. Giske, P. Heisig, A. P. MacGowan, J. W. Mouton, P. Nordmann, A. C. Rodloff, G. M. Rossolini, C. J. Soussy, M. Steinbakk, T. G. Winstanley, and G. Kahlmeter (2013), "EUCAST Expert rules in antimicrobial susceptibility testing" Clin. Microbiologie Infect. 19: 141-160. 10.1111/j.1469-0691.2011.03703.x] and/or of the French Comité de l'Antibiogramme de la Société Française de Microbiologie (CA-SFM): www.sfm-microbiologie.org. The antibiotic wafers are made of a substrate material containing a known concentration of antibiotic and suitable for diffusing it, such as blotting paper impregnated with known concentrations of antibiotic lying in the range 1 microgram (µg) to 500 µg approximately depending on the antibiotic, and they are sold by the suppliers i2a (Montpellier, France), BD (Becton Dickinson, USA), Bio-Rad (Hercules, USA), Biomerieux (Marcy l'Etoile, France).

The various antibiotic wafers used for performing an antibiogram in solid phase on agar carry the names of the antibiotics in the form of abbreviations that are standardized in the form of a code of one to three letters marked on the top face of the wafer.

The reading of results consists essentially in measuring the diameters of rings (zones in which growth of the microbial strain is inhibited). The greater the inhibition diameter, the greater the sensitivity of the bacterium to the antibiotic under test, and vice versa. The doses of the wafers are determined so as to obtain ring diameters that are proportional to the minimum inhibitory concentrations (MIC) of the antibiotic in question against the bacterium under test.

The inhibition diameter is measured in millimeters (mm) either manually with a ruler or by using a reader that enables the diameter to be read automatically. The automatic reader comprises a scanner having a camera and a detector of antibiotic wafers and of inhibition zones that are situated around these disks.

Antibiograms performed by diffusion on an agar medium are interpreted in compliance with the recommendations of the EUCAST and/or CA-SFM expert systems.

For interpretation purposes, there exist various tables or charts as a function of bacteria and antibiotics, in which there appear critical concentrations that are respectively low and high, and also critical diameters that are respectively large and small of the inhibition zone for a given concentration of said antibiotic in the wafer. Relative to each bacterium, each antibiotic presents:

a low critical concentration (and a large critical diameter) below which (and respectively above which) the bacterium is considered to be sensitive to the given antibiotic (where sensitive is marked by the letter S); and a high critical concentration (and a small critical diameter) above which (and respectively below which) the bacterium is considered as being resistant to the given antibiotic (where resistant is marked by the letter R); and between those two concentrations, the bacterium is said to be intermediate (marked by the letter I).

Thus, each bacterium is characterized relative to each antibiotic by a letter S, I, or R. In order to know whether a bacterium is resistant to a given antibiotic family, it is usually considered sufficient to test only one member of the family in order to discover its profile. Measuring an inhibition diameter thus makes it possible to interpret an antibiotic therapeutic class. Nevertheless, a single family of antibiotics is not sufficient to discover the complete phenotype of the bacterium in terms of resistance or sensitivity to various antibiotics. That is why, in an antibiogram, a plurality of antibiotics are tested by placing a plurality of wafers containing antibiotics of different classes or families or subfamilies in order to obtain a resistance or sensitivity phenotype to the various antibiotic families or subfamilies.

An antibiogram enables a doctor to select the appropriate antibiotic or association of antibiotics for treating a patient effectively.

In order to be able to discover the complete phenotype of a given bacterial strain, it is thus necessary to test different antibiotics belonging to different therapeutic classes or families or subfamilies for which the most frequent resistance mechanisms are known. The main antibiotics (with their codes in parentheses) relating to each of the following families or subfamilies are listed below:

1) family: B-lactams:
  1.1) subfamily of penicillins:
  1.1.1) penicillins of group G: Penicillin G (P),
  1.1.2) penicillins M: oxacillin (OX or OXA)
  1.1.3) penicillins of group A or aminopenicillins: amoxicillin (AMX) and ampicillin (AM);
  1.1.4) penicillins with very broad spectrum antibacterial activity:
    beta-lactamase inhibitor: an association of amoxicillin+clavulanic acid (AMC)

carboxypenicillins: ticarcillin (TIC), the association of ticarcillin+clavulanic acid (TCC), ureidopenicillins: an association of piperacillin+tazobactam (TZP), 1.2) subfamilies of cephalosporins:
1.2.1) 1st generation cephalosporins: cefalothin (CF)
1.2.2) $2^{nd}$ generation cephalosporins: cefoxitin (of the cephamycin type) (FOX), cefuroxmine (CXM)
1.2.3) $3^{rd}$ generation cephalosporins: ceftriaxone (CRO), cefotaxime (CTX), ceftazidime (CAZ),
1.2.4) $4^{th}$ generation cephalosporins of broad spectrum: cefepime (FEP), cefpirome (CPO)
1.3) subfamily of monobactams: aztreonam (ATM)
1.4) subfamilies of carbapenems: imipenem (IMP or IPM) and ertapenem (ERT)

2) family of quinolones:
2.1) $1^{st}$ generation quinolones: nalidixic acid (NA),
2.2) $2^{nd}$ generation quinolones of the fluoroquinolone type: ciprofloxacin (CIP), ofloxacin (OFX), pefloxacin (PEF), levofloxacin (LVX), moxifloxacin (MXF), norfloxacin (NOR)

3) family of aminocides: gentamicin (GEN or GM), amikacin (AK or AN), tobramycin (TOB or TM), kanamycin (K)

4) family of rifamycins: rifampicin (RA)

5) family of glycopeptides: vancomycin (VA or VAN) and teicoplanin (TEC), 6) family of sulfamides and diaminopyrimidines: the association of trimethoprim+sulfamethoxazole=cotrimoxazole (SXT), 7) family of macrolides: erythromycin (E), telithromycin (TEL)

8) family of lincosamides: lincomycin (LIN) and clindamycin (CLI or DA), 9) family of synergistines or streptogramins: pristinamycin (PT)

10) family of tetracyclines: doxycycline (DO or TE)

11) family of cyclic polypeptides or polymyxins: colistin (COL or CS)

12) family of furans: nitrofuran-furan (FT), nitrofurantoin (FUR or NT)

13) family of phenicols: chloramphenicol (C)

14) family of fucidins: fusidic acid (FA)

15) family of phosphonic antibiotics: fosfomycin (FF or FOS)

16) family of oxazolidones: linezolid (LNZ)

17) family of cyclic lipopeptides: tigecycline (TGC)

Interpreting results by using tables or charts of data specifying the critical diameters for different bacteria that correspond to the critical concentrations for the wafers containing determined concentrations of antibiotics or of an association of determined antibiotics, as issued by official associations such as the CA-SFM or EUCAST as described above is a procedure that is lengthy and complex and that represents a major constraint.

In the state of the art (1-6), various automatic techniques are known for analyzing antibiograms that involve acquiring images of the zone with diffusion disks around the antibiotics in a substrate such as a wafer by using software that calculates the diameters of said diffusion zones and compares them with the reference diameters obtained by standard methods using templates (methods specified by the National Committee for Clinical Laboratory Standards (NC-CLS)).

The object of the present invention is to provide a method that is simpler to perform and more reliable, making it possible to avoid reading and interpreting the diameters of the rings of inhibition zones around wafers one by one using criteria as specified by the CA-SFM or indeed EUCAST.

It has been found in the present invention that the images of different antibiograms can be characteristic of a phenotype and that it is possible to recognize a resistance phenotype of a bacterium relative to antibiotics by comparing photographs using a bank of photographic images of the reference antibiogram without requiring them to be interpreted in application of EUCAST or CA-SFM interpretation data; and this applies even though diameters or shapes may differ between two overall images of antibiograms of different photographs of the same phenotype; providing that for a given phenotype, a collection is available of photographs of a plurality of bacteria of the same species and of the same phenotype.

More precisely, to do this, the present invention provides a method of automatically analyzing and interpreting an antibiogram of a sample of a microorganism for analysis, preferably a bacterium, the method serving to determine a phenotype of resistance or sensitivity to at least one antimicrobial compound, preferably to a plurality of antimicrobial compounds, preferably antibiotic compounds, said phenotype being selected from a plurality of different reference phenotypes for each of the reference species of microorganism in a plurality of different species of reference microorganisms, wherein:

a) the antibiogram of the sample of the microorganism for analysis, preferably belonging to one of said species of reference microorganisms, is prepared using a determined methodology on a solid culture medium, which methodology comprises:

depositing a determined concentration of microorganism, preferably of bacterium (colony forming units per millimeter (CFU/mL)), of the sample of microorganism, preferably of bacterium, on said solid culture medium;

depositing a determined number $\underline{n}$ of a plurality of substrates, preferably n=5 to 20, more preferably n=6 to 16, on said solid culture medium, the substrates being in a determined arrangement and of a determined form, preferably in the form of wafers, each containing a determined concentration of determined antimicrobial compound(s) and suitable for diffusing one or more different determined antimicrobial compounds for each of the $\underline{n}$ said substrates; and incubating the sample of microorganism deposited on said solid culture medium under determined conditions and for a determined duration, preferably 18 h to 24 h at a temperature in the range 35° C. to 37° C.; and b) acquiring a photographic image of the antibiogram obtained in step a), preferably using a photographic image capture apparatus comprising a scanner and camera; and c) determining said phenotype of the sample of microorganism for analysis, preferably of bacterium, by using image recognition software to compare the photographic image obtained in step b) with reference images of reference antibiograms in a database made up of said reference images, such that said database comprises a plurality of at least $\underline{p}$ different reference images of antibiograms of $\underline{p}$ different strains of the same microorganism for each reference phenotype of each reference species of microorganism, preferably $\underline{p}$ being not less than 5, more preferably $\underline{p}$ being not less than 10.

Preferably, all of the reference antibiograms are prepared using the same said methodology as the antibiogram for analysis.

Preferably, said reference images and the image for analysis are taken with the same photographic image capture apparatus and under the same conditions, in particular the same distance, the same brightness, the same background, preferably a background that is flat and black, and the same resolution.

It can be understood that:
the reference antibiograms are prepared using the same said methodology as the antibiogram for analysis in terms of the number, arrangement, and form of the wafers and also the bacterial concentration and incubation conditions, except that they have wafers containing antibiotic compounds and/or antibiotic compound concentrations at least some of which are different for the various reference phenotypes; and
the reference phenotypes of the different reference strains of each species of reference bacterium in said database are determined manually by the usual standard methods by measuring the diameters of the rings of the growth inhibition zones around the antibiotic wafers, and using charts giving the critical diameter values that correspond to the critical low concentrations and the critical high concentrations for a given concentration of antibiotic in a said wafer so as to enable the bacterium of the sample under analysis to be classified as being:
sensitive to the antibiotic or combination of antibiotics contained in said wafer if the diameter of the inhibition ring surrounding the wafer is greater than the diameter corresponding to the low critical concentration;
resistant to the antibiotic or combination of antibiotics contained in said wafer if the diameter of the inhibition ring surrounding the wafer is less than the diameter corresponding to the high critical concentration; and
intermediate relative to the antibiotic or combination of antibiotics contained in said wafer if the diameter of the inhibition ring surrounding the wafer lies between the critical diameter values corresponding to the low critical concentrations and the high critical concentrations;
comparing the photographic image obtained in step b) with said reference images makes it possible to determine the phenotype of the sample of bacterium for analysis as being a said reference phenotype of a reference species of bacterium if the photographic image obtained in step b) is identical to the images of a said reference image corresponding to said reference phenotype of a reference species of bacteria, or if it is at least sufficiently similar thereto. A minimum similarity percentage may be determined experimentally using a plurality of reference images corresponding to the same phenotype of the same reference species of bacterium.

The method of the invention proceeds instantly by overall image recognition without calculating the various ring diameters as is done manually in the conventional method of interpreting antibiograms. The inventors have discovered that in spite of the fact that an inhibition ring diameter can vary within a range of values while still belonging to the same phenotype relative to the antibiotic in question, in practice, analyzing multiple zones or rings combined with multiple reference images for the same phenotype makes it possible for the antibiogram to be interpreted correctly.

Another advantage of the method of the present invention is that it makes it possible automatically to detect and take account of phenotypes presenting "synergy" between two antibiotics contained in two different wafers arranged side by side and normally resistant relative to the strain. Synergies are generated with the method on agar by the antibiotics diffusing in the agar as a result of the fact that providing the distance between two antibiotics is small enough (in the range 2 centimeters (cm) to 2.5 cm for Gram negative bacteria) they are capable of diffusing over a common portion of the agar, and as a result it is the association of the two antibiotics in this specific location that makes it possible, where appropriate, to see the appearance of a new inhibition zone, which is the synergy zone.

In the event of synergy occurring, it is possible to see mechanisms of synergy between two antibiotics since an additional inhibition zone appears generally between the two antibiotics in question. It may be in the form of an enlargement of the diameter around the disk A going towards the disk B if A and B present mutual synergy. This gives an inhibition zone of generally oval shape that is referred to as a "champagne-cork" shape between the two rings around the wafers A and B. It is possible that new synergies will be discovered in the future; the non-similarity of a synergy image, if it is new, can be detected using the method of the invention.

Preferably, in step c), said image recognition software is used to compare the shape of the outline of the rings corresponding to the inhibition zones around the substrates, and preferably also the antibiotic code letters and dosage numerals specified on the antibiotic wafers, and more preferably the software recognizes the order in which the wafers are arranged.

Software of this type is used to recognize a plant species by analyzing the image of the outline of its leaf. Also known is the image recognition software named XnView, which is freely accessible and described below, and is particularly suitable for the present invention since it thus accommodates variation in the determining characteristics, i.e. the various diameters of the various rings on either side of possible overlap between them in the form of a synergy zone.

More particularly, a minimum acceptable similarity percentage between an image for analysis and a reference image is determined, referred to below as a similarity threshold, such that the bacterium of the sample for analysis is determined as presenting a said reference phenotype of a said reference bacterium if the recognition software evaluates a similarity percentage between the image of the antibiogram of the bacterium of the sample for analysis and a reference image corresponding to said reference phenotype of said reference species of bacterium that is not less than a minimum acceptable threshold similarity percentage, preferably a minimum acceptable threshold similarity percentage of at least 70%, more preferably at least 80%.

The recognition software makes it possible to determine a said minimum acceptable similarity percentage between an image for analysis and a reference image, referred to below as the similarity threshold.

In an implementation, it is thus possible to determine a common similarity threshold applicable for all the reference phenotypes.

In another implementation, a minimum acceptable similarity percentage between said different reference images of different antibiograms of p different strains for each reference phenotype of each reference species of bacterium is determined, referred below as the reference similarity threshold, and preferably a reference similarity threshold percentage corresponding to the lowest similarity percentage between the two most different reference images for each reference phenotype of each reference species of bacteria is determined, such that the bacterium of the sample for analysis is determined as presenting a said reference phenotype of a said reference bacterium if the recognition software evaluates a similarity percentage that is not less than said reference similarity threshold between the image of the antibiogram of the bacterium of the sample for analysis and a reference image corresponding to said reference phenotype of said reference species of bacterium.

In a variant implementation, said reference phenotype is a resistance or sensitivity classification for a given antibiotic or association of antibiotics.

In this variant, the antibiogram may be an E-test, the software can read the minimum inhibitory concentration (MIC) values mentioned on the strips containing a concentration gradient of a single antibiotic, where the MIC is the value at the narrowest end of the oval ring surrounding the strip. The method of the invention thus makes it possible to avoid the errors that occur frequently when MIC is read with the naked eye by operators.

In another variant implementation, the reference phenotype is a resistance or sensitivity classification for a plurality of antibiotics and/or of associations of antibiotics, preferably in substrates in the form of wafers.

Preferably, a said reference phenotype includes a synergy phenotype between two antibiotics corresponding to two antibiotics for which the reference bacterium is resistant when they are taken separately and for which the reference bacterium is sensitive when they are taken in association. This synergy phenomenon can be recognized by the appearance of an inhibition zone in the space between two wafers corresponding to two antibiotics for which the reference bacterium is resistant.

More particularly, said reference species of bacteria are selected from more common bacteria, namely bacteria representing about 80% of the bacteria responsible for the most frequent pathologies in humans, and comprising at least *Escherichia coli, Klebsiella pneumoniae, Proteus mirabilis, Klebsiella oxytoca, Enterobacter cloacea, Enterobacter aerogenes, Entercoccus faecalis, Pseudomonas aeruginosa, Staphylococcus aureus*, and *Staphylococcus epidermidis*.

Still more particularly, the antibiograms are made using wafers comprising the following antibiotics and with the following marking corresponding to the following antibiotics: AMX for amoxicillin; AMC for amoxicillin-clavulanic acid; GEN for gentamicin; SXT for trimethoprim-sulfamethoxazole (cotrimoxazole); TIC for ticarcillin; TCC for ticarcillin-clavulanic acid; TZP for piperacillin-tazobactam; CAZ for ceftazidime; IMP for imipenem; COL or CL for colistin; FOX for cefoxitine; VAN or VA for vancomycin; TEC for teicoplanin; CLI or DA for clindamycin; CRO for ceftriaxone; FEP for cefepime; L or LIN for lincomycin; FUR or NT for nitrofurantoin; CIP for ciprofloxacin; OFX for ofloxacin; CTX for cefotaxime; AK or AN for amikacin; TOB or TM for tobramycin; FOX for cefoxitine; ATM for aztreonam; ERT for ertapenem; FF or FOS for fosfomycin; DOI for doxycycline; K for kanamycin; L or LIN for lincomycin; LNZ for linezolid; NA for nalidixic acid; NOR for norfloxacin; MET for metronidazole; MEM for meropenem; PT for pristinamycin; P for penicillin G; RA for rifampicin; TGC for tigecycline; TEL for telithromycin; E for erythromycin; and OX or OXA for oxacillin.

Still more particularly, the inventors have determined particular reference phenotypes that are more particularly appropriate for testing bacteria responsible for human pathologies that are detectable in particular in urine and that are treated by the above antibiotics, the reference phenotype being a resistance classification or selected from at least one of the following phenotypes:

phenotype referred to as "wild": bacterium that possesses no acquired resistance to antibiotics, said bacterium possibly possessing natural resistances;

phenotype referred to as "low level penicillinase": bacterium producing penicillinase capable of inhibiting bacterial growth at low antibiotic concentrations of the penicillin family, i.e. concentrations lower than 8 milligrams per liter (mg/L);

phenotype referred to as "penicillinase resistant to inhibitors": bacterium producing penicillinase that is resistant to all penicillinase inhibitors that are considered capable of inactivating this enzyme;

phenotype referred to as "high level penicillinase": bacterium producing penicillinase capable of inhibiting bacterial growth at high antibiotic concentrations of the family of penicillins, i.e. concentrations higher than 8 mg/L;

phenotype referred to as "broad spectrum beta-lactamase" (BSBL): bacterium producing beta-lactamase;

phenotype referred to as "high level cephalosporinase": bacterium producing cephalosporinase capable of inhibiting bacterial growth at high antibiotic concentrations of the cephalosporin family, i.e. concentrations higher than 2 mg/L;

phenotype referred to as "carpanesemase": bacteria producing carpanesemase;

phenotype referred to as "selective permeability to imipenem": bacteria possessing intermediate sensitivity with respect to imipenem;

"resistant to methicillin" (previous name for a penicillin of group M, now replaced by oxacillin which is a penicillin belonging to the subfamily of penicillins of group M) bacterium resistant to methicillin (=resistant to oxacillin) by acquiring a new target having no affinity for B-lactamines (penicillin binding protein 2a (PLP2a));

phenotype referred to as "resistance to fluoroquinolones": bacterium for which growth is not inhibited in the presence of antibiotic compounds of the fluoroquinolone family;

phenotype referred to as "resistance to aminosides": bacterium for which growth is not inhibited in the presence of antibiotic compounds of the aminoside family;

phenotype referred to as "resistance to macrolides": bacterium for which growth is not inhibited in the presence of antibiotic compounds of the macrolide family;

phenotype "resistance to cotrimoxazole": bacterium for which growth is not inhibited in the presence of cotrimoxazole;

phenotype referred to as "resistance to rifampicin": bacterium for which growth is not inhibited in the presence of rifampicin; and phenotype referred to as "atypical phenotype": phenotype that is not known or that cannot be determined.

Penicillinase is an enzyme capable of destroying (hydrolyzing) penicillin and making it inactive relative to the bacterium.

Cephalosporinase is an enzyme capable of destroying (hydrolyzing) cephalosporins and of making them inactive relative to the bacterium.

Carbapenemase is an enzyme capable of destroying (hydrolyzing) carbapenems and of making them inactive relative to the bacterium.

Beta-lactamase is an enzyme capable of hydrolyzing penicillins, cephalosporins, and monobactams such as astreonam, but not carbapenems nor cephamycins such as cefoxitine.

Still more particularly, the antibiogram under analysis and/or said database comprises the reference phenotypes for the reference species of bacteria corresponding to the following resistances (I, R) or sensitivities (S) relative to concentrations of six antibiotic compounds selected from the following groups a1) to a6), preferably arranged in a circle in the following order for each group:
- a1) AMX, AMC, TCC, CRO, FEP, and IMP,
- a2) AMX, AMC, TZP, CRO, FEP, and IMP,
- a3) AMC, TZP, CRO, FEP, IMP, and COL,
- a4) AMX, GEN, LIN, FUR, VAN, and TEC,
- a5) TIC, TCC, TZP, FEP, CAZ, and IMP, and
- a6) FOX, CLI, SXT, GEN, VAN, and TEC.

These groups a1) to a6) are more particularly pertinent with respect to the following phenotypes for the above-listed bacteria:
- phenotype "wild",
- phenotype "low level penicillinase",
- phenotype "penicillinase resistant to inhibitors",
- phenotype "high level penicillinase",
- phenotype "broad spectrum beta-lactamase" (BSBL),
- phenotype "high level cephalosporinase",
- phenotype "carbapenemase",
- phenotype "selective permeability to imipenem",
- "resistant to methicillin", and
- phenotype "atypical phenotype".

Still more particularly, the antibiogram under analysis and/or said database comprises the following reference phenotypes for the following reference species of bacteria corresponding to the following resistances (I/R) or sensitivities (S) with respect to sixteen antibiotic compounds selected from the following groups b1) and b2), preferably having their wafers arranged in a rectangular grid in the following order starting from the first row on the right with four rows of four compounds aligned in columns for each group:
- b1) CIP, OFX, TIC, COL, IMP, CTX, TCC, AK, SXT, AMC, CRO, TOB, AMX, ATM, FOX, and GEN, and
- b2) SXT, DA, FOX, OXA, PT, GEN, CIP, RA, TEC, VAN, LNZ, FF, TOB, E, DO, and NT.

These groups b1) and b2) are more particularly pertinent with respect to the following phenotypes for the bacteria listed above:
- phenotype "wild",
- phenotype associating "high level penicillinase"+"resistance to fluoroquinolones"+"resistance to cotrimoxazole"+"resistance to aminosides", and
- phenotype associating "cephalosporinase"+"resistance to fluoroquinolones"+resistance to cotrimoxazole"+"resistance to aminosides", and
- phenotype associating "cephalosporinase"+"resistance to cotrimoxazole"+"resistance to aminosides", and
- phenotype associating "resistance to methicillin"+"resistance to fluoroquinolones"+"resistance to rifampicin"+ "resistance to macrolides"+"resistance to aminosides".

The above sixteen-wafer reference phenotypes are more particularly useful for so-called "deep" infections such as septicemias, for example.

Still more particularly, in step a), the reference antibiograms and the antibiogram of the sample of bacterium for analysis are prepared using a determined methodology on a solid culture medium of Mueller-Hinton agar type comprising:
- a number (n) of six to sixteen wafers in the form of disks having antibiotic concentrations in the range 10 µg to 300 µg, arranged in a circle or a rectangular grid;
- a determined bacterial concentration (CFU/mL) of the sample for analysis or of the reference deposited on said solid culture medium, corresponding to a deposited suspension having opacity matching the 0.5 standard in the McFarland range; and
- determined incubation conditions and duration preferably of 18 h to 24 h at 37° C.

Still more particularly, the wafers are arranged in a circle of six on a culture medium or on a regular grid in dishes of square shape, preferably having 16 squares.

Other characteristics and advantages of the present invention appear better on reading the following description given by way of non-limiting illustration and with reference to the accompanying drawings, in which:

FIG. 1A shows the overall outline of the set of inhibition zones 1 to 6 in the image of FIG. 1B;

FIGS. 4A and 4B are photographs of antibiograms of phenotypes that are not recognized as belonging to the same phenotype by the method of the invention, FIG. 4A showing a strain of *E. coli* that is sensitive to all antibiotics, while FIG. 4B shows a strain of *E. coli* that is resistant to all antibiotics;

Figure 5:
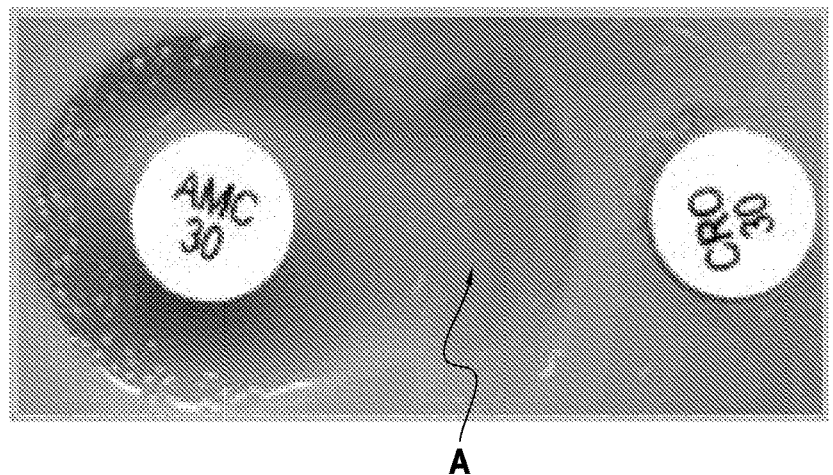
Figure 6A:
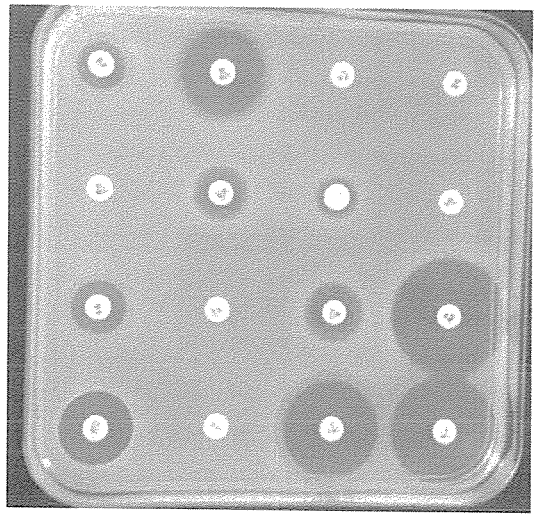
Figure 6B:
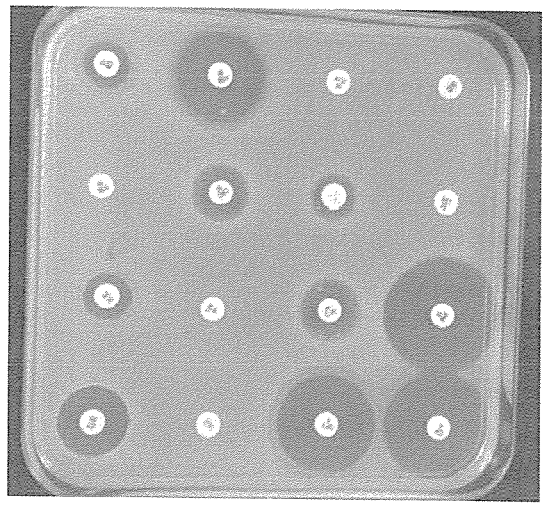

FIG. 5 is an image of a synergy zone in the shape of a champagne cork (A) for an *E. coli* strain of BSBL phenotype between two wafers, one of AMC and the other of CRO; and FIGS. 6A and 6B are photographs of antibiograms arranged in a square for two strains of *K. pneumoniae* of the same cephalosporinase phenotype and recognized as such with a similarity percentage of 88% by the method of the invention.

The current recommendations of expert committees are booklets of about 100 pages comprising SIR interpretations for tens of antibiotics on the more common species of bacteria. For a given antibiotic class, a biologist can decide to test one or more antibiotics as proposed in those recommendations. In practice, only a few antibiotics are antibiotics that are key for interpretation and above all that are useful for a clinician, who for example might use only one molecule in the list if it is desired to use penicillin for treating a patient. In the illustrative example below, the inventors have determined six antibiotics that are representative of the others in order to determine certain phenotypes of the ten bacteria that are the most widespread in human pathology.

1) Preparing the antibiogram.

The antibiograms were prepared using the following standard methodology.

1.1) Preparing a sample of bacteria

The inoculum was prepared by making a suspension of bacteria directly from colonies put into solution in tubes of sterile water so that the solution presented accurate opacity as determined with a spectrophotometer equivalent to the opacity of a 0.5 standard in the McFarland range. This bacterial suspension concentration is standardized since a more concentrated inoculum would lead to smaller diameters for the inhibition zone, and vice versa.

The inoculum corresponds to concentrations of about 108 CFU/mL for *Escherichia coli, Klebsiella pneumoniae, Proteus mirabilis, Klebsiella oxytoca, Enterobacter cloacea, Enterobacter aerogenes, Entercoccus faecalis, Pseudomonas aeruginosa, Staphylococcus aureus,* and *Staphylococcus epidermidis.* These are the ten species bacteria that are encountered the most frequently in human pathologies.

1.2) The bacterial sample was deposited on a solid culture medium in a petri dish having a diameter of 90 mm or in a square dish having a side of 120 mm, the medium being constituted by a Mueller-Hinton agar specific for (EUCAST) antibiograms. Ideally, it should be used in the 15 minutes (min) following preparation of the suspension.

Seeding was done by the method of diffusion on an agar medium by flooding in which excess bacterial suspension was added to the Mueller-Hinton agar. After homogenizing, excess liquid was discarded in order to avoid over-inoculating the dishes. It is necessary to wait beforehand for the surface of the agar to be dry in order to eliminate any trace of moisture encouraging bacterial invasion.

The disks of the antibiotic wafers were deposited within 15 min after inoculating the agar. The antibiotic impregnated disks were deposited using an automatic dispenser that placed the disks firmly on the surface of the inoculated and dried agar. The number of disks deposited per dish was limited because of inhibition zone overlap and in order to limit interference between antibiotics. It is important for the inhibition diameters to be measurable. The antibiograms were then incubated at 37° C. for 18 hours (h) to 24 h.

The antibiotic wafers were made of high quality absorbent paper with a diameter of 6 mm and they were impregnated with antibiotics at concentrations in the range 1 micrograms (μg) to 300 μg approximately, depending on the antibiotic.

In the examples below, reference disks were used as sold by the suppliers i2a (Montpellier, France), BD (Becton Dickinson, USA), Bio-Rad (Hercules, USA), Biomerieux (Marcy l'Etoile, France) containing the following antibiotics and carrying the following codes and the following doses: AMX (amoxicillin) 25 μg: AMC (amoxicillin-clavulanic acid) 20 μg-10 μg; GM for gentamicin, 15 μg; SXT (trimethoprim-sulfamethoxazole) 1.25/23.75 μg; TIC (ticarcillin) 75 μg; TCC (ticarcillin-clavulanic acid) 75/100 μg; TZP (piperacillin-tazobactam) 75/10 μg; CAZ (ceftazidime) 30 μg; IMP or IPM (imipeneme) 10 μg; COL (colistin) 50 μg; FOX (cefoxitine) 30 μg; VAN (vancomycin) 30 μg; TEC (teicoplanin) 30 μg; CLI or DA (clindamycin) 2 μg; CRO (ceftriaxone) 30 μg; CIP (ciprofloxacin) 5 μg; OFX (ofloxacin) 5 μg; CTX (cefotaxime) 5 μg; AN or AK (amikacin) 30 μg; TM (tobramycin) 10 μg; FOX (cefoxitine) 30 μg; ATM (aztreonam) 30 μg; ERT (ertapenem) 10 μg; FF (fosfomycin) 200 μg; DO (doxycycline) 30 μg; K (kanamycin) 1000 μg; L (lincomycin) 15 μs; LNZ (linezolid) 10 μg; AN (nalidixic acid) 30 μg; NOR (norfloxacin) 10 μg; PT (pristinamycin) 15 μg; RA (rifampicin) 5 μg; and E (erythromycin) 15 μg.

More precisely, the agar was prepared as follows:

the agar were seeded with 1 milliliter (mL) of suspension and the volume was spread with a spreader from the center to the edges until the entire surface had been seeded:

it was allowed to dry for 3 min to 5 min;

the antibiotic disks were put into place on the bottom of the dish (at some minimum distance from the edge); by subdividing the dish into as many subdivisions as there were wafers (a maximum of six in a circle for a 90 mm dish, or 16 for a 120 mm dish), i.e. regularly spaced-apart around a circle at a spacing of 2.5 cm for round dishes or on a rectangular grid at a spacing of 3 cm for square dishes; and incubation for 18 h to 24 h at 37° C.

2) Reading and interpreting the antibiograms:

After the incubation period, rings can be seen to appear around the antibiotic disks. These zones correspond to the inhibition diameters for bacterial growth. For each antibiotic present on the agar, as a result of the antibiotic concentration gradient, there is a zone in which growth is inhibited, as explained above. The inhibition rings appear darker since the photographs were taken on a black background so contrast is at its greatest in those zones where there was no bacterial growth.

In order to set up a bank of reference antibiograms suitable for constituting a reference image database of reference phenotypes for the reference bacteria, the diameters of the rings were measured manually and tables and charts were used in order to interpret them, as set out in Table A below.

2.1) Taking *Escherichia coli* as an example, it is desired for example to discover its sensitivity relative to various carbapenems including imipenem, and the recommendations of EUCAST [1] and of CA-SFM can be found in the table below:

TABLE A

| Carbapenems | Critical concentrations (mg/L) | | Disk load (μg) | Critical diameters (mm) | |
|---|---|---|---|---|---|
| | S≤ | R> | | S≤ | R> |
| Doripenem | 1 | 2 | 10 | 24 | 21 |
| Ertapenem | 0.5 | 1 | 10 | 25 | 22 |
| Imipenem | 2 | 8 | 10 | 22 | 16 |
| Meopenem | 2 | 8 | 10 | 22 | 16 |

For a dose of 10 μg of antibiotic, the critical diameters in mm lie in the range <16 mm to 22 mm, which means that if the diameter is greater than or equal to 22 mm, then the strain is sensitive to imipenem, if the diameter lies in the range 16 mm to less than 22 mm, the strain possesses intermediate sensitivity to the antibiotic in question, and if the diameter is less than 16 mm, the strain is resistant to imipenem.

2.2) Thus, with 206 bacterial samples of reference bacteria and antibiotic wafers as listed in Table B below (six wafers having six different antibiotics), a reference bank of bacterial samples was prepared having the following reference phenotypes as listed in Table C1 below.

TABLE B

| Bacterium (number of strains) | Panel of six antibiotics at fixed concentrations | | | | | |
|---|---|---|---|---|---|---|
| E. coli (42) | AMX | AMC | TCC | CRO | FEP | IMP |
| P. mirabilis (16) | 25 μg | 20/10 μg | 75/10 μg | 30 μg | 30 μg | 10 μg |

TABLE B-continued

| Bacterium (number of strains) | Panel of six antibiotics at fixed concentrations | | | | | |
|---|---|---|---|---|---|---|
| K. pneumonia (38) | AMC | TZP | CRO | FEP | IMP | COL |
| K. oxytoca (6) | 20/10 μg | 75/10 μg | 30 μg | 30 μg | 10 μg | 50 μg |
| E. cloacae (8) | | | | | | |
| E. aerogenes (11) | | | | | | |
| P. aeruginosa 35) | TIC | TCC | TZP | FEP | CAZ | IMP |
| | 75 μg | 75/10 μg | 75/10 μg | 30 μg | 30 μg | 10 μg |
| E. faecalis (17) | AMX | GEN | LIN | FUR | VAN | TEC |
| | 25 μg | 15 μg | 15 μg | 300 μg | 30 μg | 30 μg |
| S. aureus (25) | FOX | CLI | SXT | GEN | VAN | TEC |
| S. epidermidis (8) | 30 μg | 2 μg | 1.25/23.75 μg | 15 μg | 30 μg | 30 μg |

Table C1 lists various reference phenotypes for the reference bacterial species under test corresponding to their resistances or sensitivities relative to the antibiotics, in which:

the phenotypes and the antibiotic codes have the meanings given above;

S means: sensitive to the antibiotic or to the combination of antibiotics contained in said wafer, the diameter of the inhibition ring surrounding the wafer being greater than the diameter corresponding to the low critical concentration;

R means: resistance to the antibiotic or the combination of antibiotics contained in said wafer, the diameter of the inhibition ring surrounding the wafer being less than the diameter corresponding to the high critical concentration; and I means: intermediate relative to the antibiotic or the combination of antibiotics contained in said wafer, the inhibition ring diameter surrounding the wafer lying between the critical diameter values corresponding to the low critical concentration and to the high critical concentration.

Said database contains the reference phenotypes for the reference species of bacteria corresponding to resistance (I, R) or sensitivity (S) as follows with respect to the concentrations of six antibiotic compounds as mentioned in Table C1:

| Bacteria | Phenotypes | Antibiotics | | | | | |
|---|---|---|---|---|---|---|---|
| E. coli | | AMX | AMC | TCC | CRO | FEP | IMP |
| | Wild | S | S | S | S | S | S |
| | Ll penicillinase | R | S | S | S | S | S |
| | Inhibitor resistant penicillinase | R | R | R | S | S | S |
| | Hl penicillinase | R | I/R | I/R | S | S | S |
| | BSBL | R | R | R | R | R | S |
| | Hl cephalosporinase | R | R | R | R | R | S |
| | Carbapenemase | R | R | R | R | R | R |
| P. mirabilis | | AMX | AMC | TCC | CRO | FEP | IMP |
| | Wild | S | S | S | S | S | S |
| | Ll penicillinase | R | S | S | S | S | S |
| | Inhibitor resistant penicillinase | R | R | R | S | S | S |
| | Hl penicillinase | R | I | I | S | S | S |
| | Hl cephalosporinase | R | R | R | R | R | S |
| K. pneumoniae | | AMC | TZP | CRO | FEP | IMP | COL |
| | Wild | S | S | S | S | S | S |
| | Ll penicillinase | S | R | S | S | S | S |
| | Hl penicillinase | I/R | S/I/R | I | S | S | S |
| | BSBL | R | R/I | I/R | R | S | S |
| | Hl cephalosporinase | I/R | I/R | I/R | S | S | S |
| | Carbapenemase | R | R | R | R | R | S |
| K. oxytoca | | AMC | TZP | CRO | FEP | IMP | COL |
| | Wild | S | S | S | S | S | S |
| E. faecalis | | AMX | GEN | LIN | FUR | VAN | TEC |
| | Wild | S | S | S | S | S | S |
| | Atypical | R | S | S | S | S | S |
| E. aerogenes | | AMC | TZP | CRO | FEP | IMP | COL |
| | Wild | S | S | S | S | S | S |
| | BSBL | R | R | R | R/I | S | S |
| E. cloacae | | AMC | TZP | CRO | FEP | IMP | COL |
| | Wild | S | S | S | S | S | S |
| | BSBL | R | R | R | R | S | S |
| P. aeruginosa | | TIC | TCC | TZP | FEP | CAZ | IMP |
| | Wild | S | S | S | S | S | S |
| | Selective imipenem permeability | S | S | S | S | S | I |
| | Penicillinase | R | I/R | I/S | S | S | S |
| | BSBL | I/R | I/R | I/R | I/R | R | S |
| | Carbapenemase | R | R | R | R | R | R |
| | Abnormal phenotype | R | R | R/S | R | S | S |

-continued

| Bacteria | Phenotypes | Antibiotics | | | | | |
|---|---|---|---|---|---|---|---|
| S. aureus | | FOX | CLI | SXT | GEN | VAN | TEC |
| | Wild | S | S | S | S | S | S |
| | Methicillin resistant | R | R/S | S | S | S | S |
| S. epidermidis | | FOX | CLI | SXT | GEN | VAN | TEC |
| | Wild | S | S | S | S | S | S |
| | Methicillin resistant | R | R/S | S | S | S | S |

The wafers of Table C1 above were arranged successively in a circle on the antibiograms with the order of the columns from left to right in the table corresponding to clockwise order around the circle.

The BSBL phenotype includes a synergy phenotype between ceftriaxone and clavulanic acid, and thus between CRO and TCC or AMC (for all of the BSBL bacteria in the table).

2.3) The inventors have verified that the software can also recognize antibiograms prepared on square dishes with a larger number of antibiotics. They have prepared twenty-five antibiograms of sixteen wafers comprising: AMX 25 µg; AMX 20 µg-10 µg; GM or GEN 15 µg; SXT 1.25 µg/23.75 µg; TIC 75 µg; TCC 75 µg/10 µg; IMP or IPM 10 µg; COL 50 µg; CRO 30 µg; CIP 5 µg; OFX 5 µg: CTX 5 µg; AN or AK 30 µg; TOB 10 µg; FOX 30 µg; ATM 30 µg, CLI or DA 2 µg, 30 µg, 30 µg, VA or VAN 30 µg, FF 200 µg, E 15 µg, NT or FUR 300 µg, PT 15 µg, TEC 30 µg, LNZ 10 µg.

The said database comprises the following reference phenotypes or the following reference species of bacteria corresponding to resistant (I/R) or sensitive (S) as follows with respect to the 16 antibiotics mentioned in Table C2 below for which the wafers were arranged in a rectangular grid in the following order starting from the first row on the right with four rows of four compounds aligned in columns for each group:

The above reference phenotypes with sixteen wafers are more particularly useful for so-called "deep" infections such as septicemias, for example.

3) Reference image bank and interpretation in accordance with the invention by comparing photographic images of antibiograms.

3.1) The photographs were taken with an image capture apparatus comprising a Scan®1200 Interscience ref. 437 000 scanner from Interscience, France.

Images were taken in standardized manner using a high resolution scanner with the dish for photographing placed in the scanner and the brightness, the height, and the quality of the photographs in pixels being the same on each occasion. Each photograph was taken under the same conditions:
- flat black background
- same light/same brightness adjusted automatically by the software with six white light combinations below and/or above against a black background
- the same image capture apparatus: Scan®1200 Interscience ref. 437 000
- same distance of 10 cm
- same scale in the range 1.5 to 3.

It provided photographs having a resolution of at least 1280×960 pixels.

3.2) Initially the inventors were seeking merely to standardize the number of antibiotics by limiting that number to

TABLE C2

| Bacteria | Phenotypes | Antibiotics | | | | | | | |
|---|---|---|---|---|---|---|---|---|---|
| E. coli | Wild | CIP | OFX | TIC | COL | IPM | CTX | TCC | AK |
| | | S | S | S | S | S | S | S | S |
| | | SXT | AMC | CRO | TOB | AX | ATM | FOX | GEN |
| | | S | S | S | S | S | S | S | S |
| | Hl penicillinase + R to fluoroquinolones + R to cotrimoxazole + partial R to aminosides | CIP | OFX | TIC | COL | IPM | CTX | TCC | AK |
| | | R | R | R | S | S | S | I | S |
| | | SXT | AMC | CRO | TOB | AX | ATM | FOX | GEN |
| | | R | I | S | R | R | S | S | R |
| | Cephalosporinase + R to fluoroquinolones + R to cotrimoxazole + partial R to aminosides | CIP | OFX | TIC | COL | IPM | CTX | TCC | AK |
| | | R | R | R | S | S | R | R | S |
| | | SXT | AMC | CRO | TOB | AX | ATM | FOX | GEN |
| | | R | R | R | R | R | R | S | R |
| K. pneumoniae | Wild | CIP | OFX | TIC | COL | IPM | CTX | TCC | AK |
| | | S | S | R | S | S | R | R | R |
| | | SXT | AMC | CRO | TOB | AX | ATM | FOX | GEN |
| | | R | R | R | R | R | R | S | R |
| | Cephalosporinase + R to aminosides + R to cotrimoxazole | CIP | OFX | TIC | COL | IPM | CTX | TCC | AK |
| | | R | R | R | S | S | R | R | S |
| | | SXT | AMC | CRO | TOB | AX | ATM | FOX | GEN |
| | | R | R | R | R | R | R | S | R |
| S. aureus | Wild | SXT | DA | FOX | OXA | PT | GEN | CIP | RA |
| | | S | S | S | S | S | S | S | S |
| | | TEC | VA | LNZ | FF | TOB | E | DO | NT |
| | | S | S | S | S | S | S | S | S |
| | R to methicilline, R to aminosides, fluoroquinolones, to rifampicie, to macrolides and the like . . . | SXT | DA | FOX | OXA | PT | GEN | CIP | RA |
| | | R | R | R | R | R | R | R | R |
| | | TEC | VA | LNZ | FF | TOB | E | DO | NT |
| | | S | S | S | R | R | R | R | R | a small value, in particular to only six antibiotics in a single dish for the commonest bacteria. That led them to test the reproducibility and the repeatability of the technique on a large number of samples in order to be able to automate it. For that purpose, they took photographs of all of the results and thus built up a data bank with those images. From that large number of photographs, they compared them with one another and happened to observe that photographs of each phenotype, appeared to be mutually recognizable even though they were distinct. In other words, it appeared to be possible to recognize the phenotype of a bacterium on the basis of a general image of the antibiogram without directly measuring the inhibition diameters on the antibiogram and without needing to interpret them using EUCAST interpretation data.

Thereafter, they sought to confirm this recognition by using automatic image recognition software. For that purpose, they made use of XnView image recognition software that can be downloaded on-line ((http://www.xnview.com/fr/, Gougelet Pierre-Emmanuel, 10 rue Rene de Chateaubriand, La Neuvilette 51100 Reims, France). That software makes it possible to create image bank directories and then to search the computer on which it is installed for similar images in targeted manner (in a different directory), or in all of the storage disks of the computer. The software is thus not subjected to "interference" by images that have nothing to do with the search in question.

The software also gives a similarity percentage for photographs compared with photographs in the image bank. Each photograph corresponds to a leaf that has been scanned. The leaves were scanned by the scanner in order to obtain green leaves on a white background and in order to enable the leaf to be segmented simply. Thereafter, the color of the image was converted into a gray scale. The binary outlines of the image were traced by sequential analysis. If a pixel is found, the software searches the limits closest to the point in order to identify the outline only. Only the longest boundary of the image is taken into account, with the other boundaries between two objects and holes being considered as constituting noise.

Figure 1A:
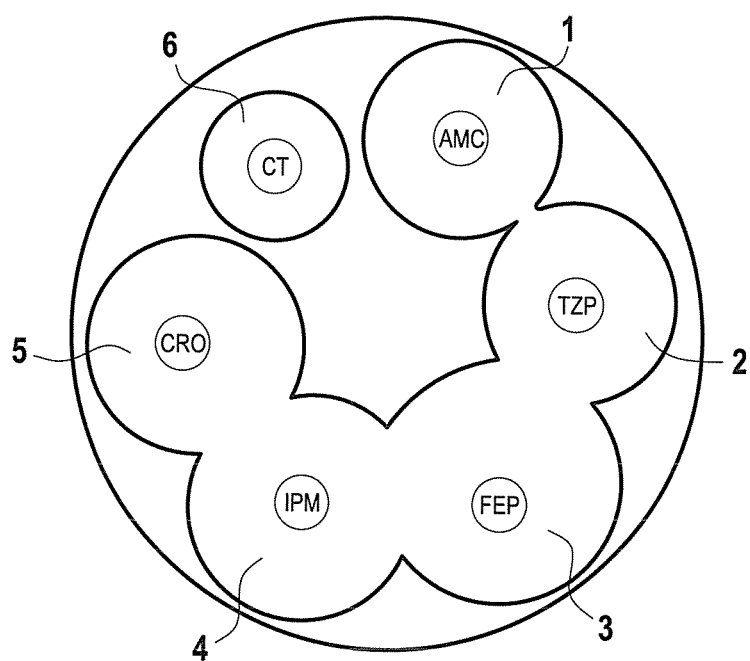
FIGS. 1A and 1B show the principle of recognizing an overall image outline in an antibiogram.
Figure 1B:
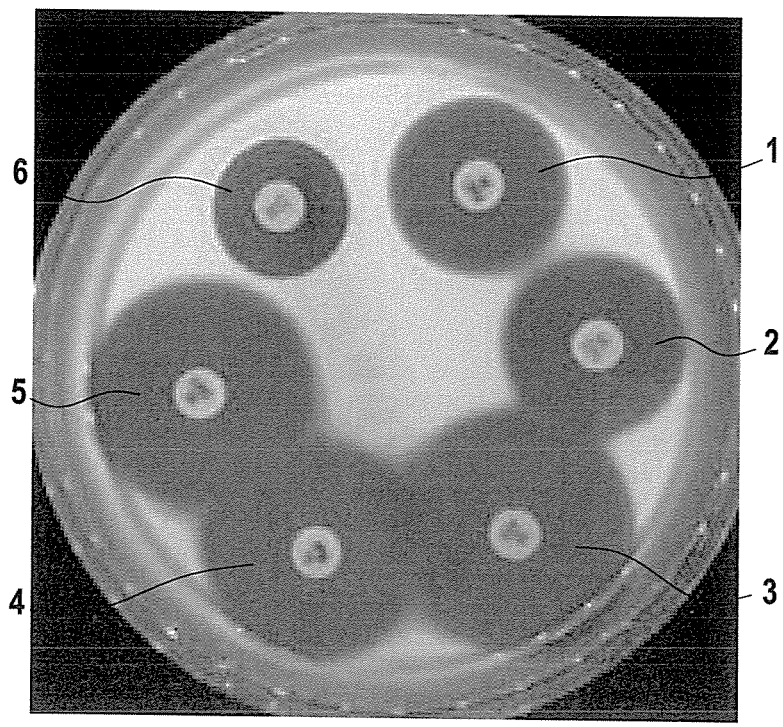

Such software was found to be suitable for recognizing photographs of antibiograms since only the inhibition diameters vary from one phenotype to another, which gives rise to a variation in the outline of the overall image of the antibiogram, as shown in FIGS. 1A and 1B. The software is thus capable of recognizing indirectly the various inhibition diameters and of producing the phenotype interpretations thereof by comparing the image of the antibiogram as a whole.

The image recognition software compares a photograph of an antibiogram for analysis with the reference images of the image bank as prepared from the reference antibiograms, and in practice it is capable of recognizing photographs of strains that present similarity or resemblance of at least 70%, thereby giving the reference phenotype that corresponds to the tested sample, if there is one. If the image is recognized by the software with similarity of at least 70% relative to a reference image, that means that the bacterium possesses the same phenotype as the reference image, and the software can thus give it its phenotype.

Another piece of software developed for recognizing images such as photographs of leaves of certain plants and to deduce therefrom the species of the plant (P. Novotny, T. Suk (2013), Leaf recognition of woody species in central Europe, J. Clin. Microbiol.) is also capable of recognizing photographs of antibiograms in comparison with photographs to be found in an existing data bank constituted beforehand. More particularly, that software is capable of using leaves to recognize the species of a tree by referring to a leaf data bank with a plurality of photographs of leaves for a given species, with this being done by comparing solely the outlines of leaves without taking into consideration anything that lies inside or outside the outlines, and it determines the species of the tree by analogy in the shapes of outlines.

It is then possible to provide therapeutic recommendations automatically at the same time as the phenotype during validation so that the clinician possesses all of the data.

Thus, by way of example for *E. coli*, the inventors began by creating a directory of photographs from photographs of antibiograms of 42 clinical isolates of *E. coli*. In those 42 photographs, they selected several for each given phenotype. Each of the photographs was given a new name as a function of its phenotype and the software was asked whether it could recognize other phenotypes similar to the reference phenotype and to discover the percentage of similarity from which the software began to make errors concerning the recognition of phenotype.

By reducing the similarity percentage progressively in steps of 5%, it was found that the minimum similarly percentage needed is 70% for that software in order to recognize, without error, photographs of different antibiograms but for the same phenotype.

Figure 2A:
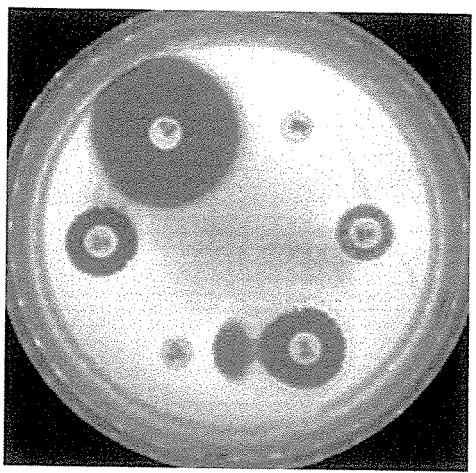
FIGS. 2A to 2C are photographic images of antibiograms of *E. coli* strains of BSBL phenotypes recognized as belonging to the same phenotype with a similarity percentage in the range 87% to 100% by the method of the invention.
Figure 2B:
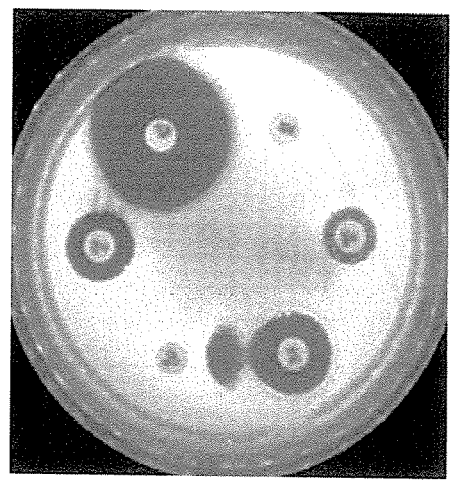
Figure 2C:
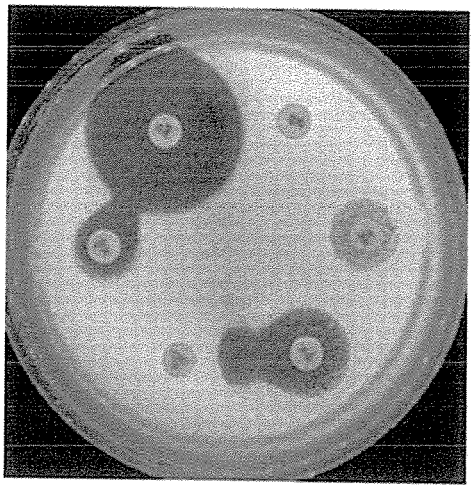

FIGS. 2A to 2C show the fact that the XnView image recognition software is capable of giving the correct phenotype of BSBL phenotype *E. coli* bacteria with a similarity of:

100% between the images of FIGS. 2A and 2B; and
87% between the images of FIGS. 2A and 2C.

Figure 2D:
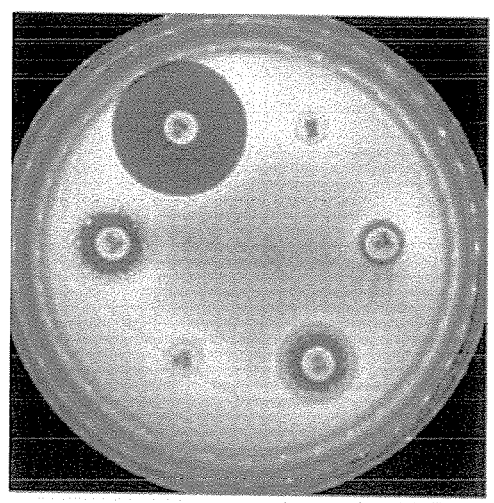
FIGS. 2D and 2E are photographic images of antibiograms of *E. coli* strains of cephalosporinase phenotypes recognized as belonging to the same phenotype with a similarity percentage of 75% by the method of the invention.
Figure 2E:
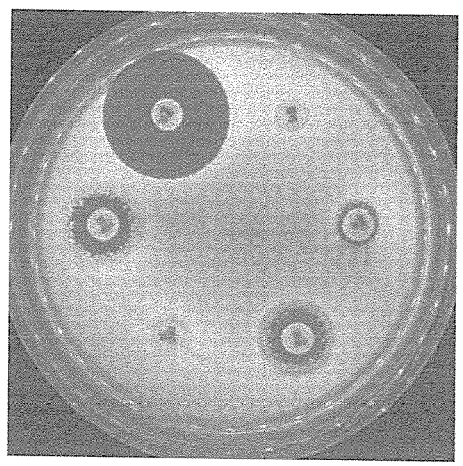

FIGS. 2D and 2E illustrate the fact that the XnView image recognition software is capable of giving the correct phenotype for cephalosporinase phenotype *E. coli* bacteria with a similarity of:

74% for the images of FIGS. 2D and 2E, and
65% between the images of FIGS. 2A and 2D which differ essentially by the presence of a zone of synergy between AMX and TCC for BSBL (FIGS. 2A to 2C) and the absence of a zone of synergy between AMX and TCC for the cephalosporinase phenotype.

Figure 3A:
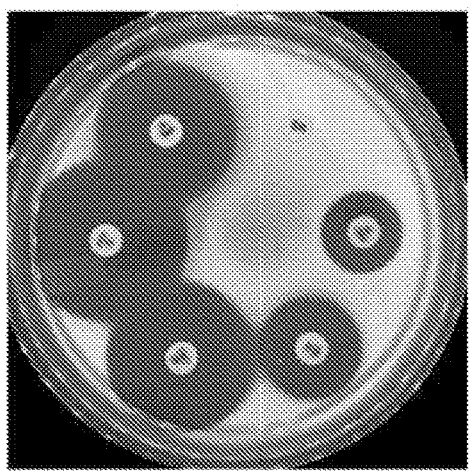
FIGS. 3A and 3B are two photographs of antibiograms of *Escherichia coli* strains that produce high level penicillinases and recognized as such with a similarity percentage of 80% by the method of the invention.
Figure 3B:
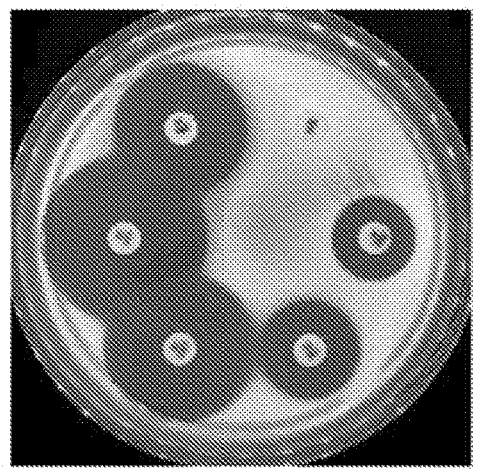

FIGS. 3A and 3B show that the software is capable of recognizing photographs of antibiograms presenting the same "high level penicillinase" phenotype for *E. coli* bacteria from a database of 42 photographs of 42 samples of *E. coli* presenting various phenotypes and with similarity of 80%.

Figure 4A:
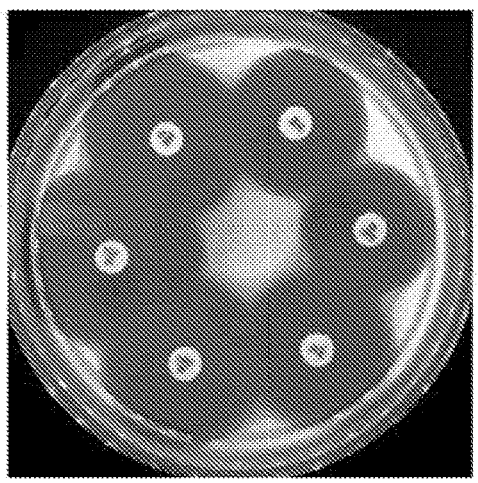
Figure 4B:
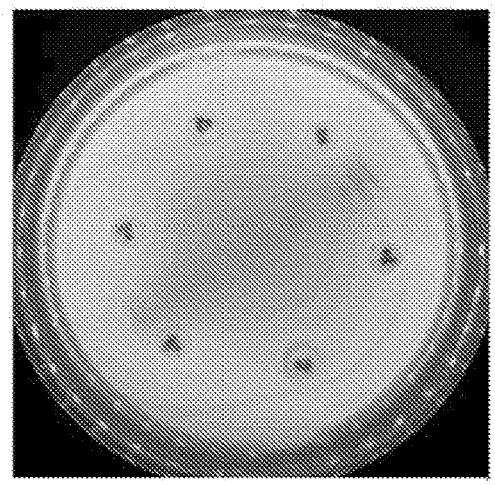

FIGS. 4A and 4B are photographs of antibiograms of two strains of *Escherichia coli*: the strain of FIG. 4A is sensitive to all of the tested antibiotics (wild strain), while the strain of FIG. 4B is resistant to all of the antibiotics.

FIG. 5 shows that it is possible to interpret a very particular resistance mechanism by images of synergy showing up synergetic mechanisms between two antibiotics.

In FIG. 5, an *E. coli* bacterium having a mechanism for resistance to broad spectrum B-lactamase (BSBL) antibiotics presents synergy between two particular antibiotics: ceftriaxone (3rd generation cephalosporin of the b-lactam family) and the association of amoxicillin+clavulanic acid (amoxicillin is an aminopenicillin+a b-lactam inhibitor). This synergy can be seen directly on the agar since a small inhibition zone appears having a "champagne-cork" shape between the two wafers of those antibiotics placed side by side and which are normally resistant to this strain. Recognizing the overall image of the antibiogram enables this type of synergistic mechanism between two antibiotics to be identified.

The inventors have verified that the software can also recognize antibiograms prepared with square dishes and having a larger number of antibiotics. They have prepared twenty-five antibiograms of sixteen wafers, each having the various phenotypes described above.

FIGS. 6A and 6B show that the software is capable of recognizing photographs of antibiograms presenting the same phenotype ("cephalosporinase+resistance to aminosides and to cotrimoxazole") of *K. pneumoniae* bacteria from a database of nine photographs of nine samples of *K. pneumoniae* presenting varying phenotypes with similarity of 88%.

The software is capable of recognizing the photographs as being photographs of the same reference bacterium having the same phenotype with a similarity of at least 70%.

This similarity ratio guarantees recognition of the color, the letters of the antibiotic codes, and the numbers of the concentration doses marked on the disks, and the outlines of the image of the rings. Each antibiotic deposited on the agar possesses a two- or three-letter code for identifying it (corresponding to an abbreviation of its name) and for verifying that the antibiotic present on the agar is indeed the right antibiotic. The dosage of the antibiotic is also marked. For example, on the disk of imipenem there can be seen the code "IPM 10 µg", which corresponds to a disk of imipenem with a 10 µg dose. Finally, the software recognizes that the arrangement of the wafers in a circle or in a square is correct.

The outlines and the shape of the image are two different things. The shape of the image comprises the overall shape of the image, whereas the outlines of the image in this description refer to a single portion of the image, such as for example solely the outlines of the inhibition zones, as can be seen in FIGS. 1A and 1B.

Given that for a single phenotype the diameter can vary (cf. above, e.g. over the range 16 mm to 22 mm for I and R if >16, or S if >22), the greater the number of reference images for the same phenotype in the database, the better the recognition of that phenotype, even if the diameter differs a little without changing the interpretation.

On the basis of a data bank of known images, the software is capable of searching simultaneously for the images that are the most similar in a manner that is fast regardless of the quantity of images in the data bank. In addition, software can automatically generate a complete interpretation together with an analysis report and therapeutic recommendations of various kinds (comments, etc., depending on the recommendations of the committees of experts).

The use of the software comprises the following steps:
a) selecting a file containing a photograph of an antibiogram to be analyzed;
b) selecting from tools: "search for similar files" so as to enable image recognition to take place;
c) selecting the file containing the bank of reference images for comparison with the image that is to be analyzed; and
d) specifying the similarity percentage, e.g. a similarity percentage of 73%.

The comparison is such that each pair of images produces a calculated similarity value, and if this value is greater than the minimum tolerance of 73%, then the pair is considered as being similar and the two images belong to the same reference phenotype.

The reference image bank may be extended to all bacteria that are frequently found in humans, namely about 200 different species of bacteria, or indeed to all bacteria (about 2000 species that have been isolated at least once in humans).

Adding reference images serves to improve interpretation and enables the similarity threshold percentage to be increased for a given phenotype.

BIBLIOGRAPHIC REFERENCES

1) Journal of Clinical Microbiology, 1998 pages 302-304, Volume 36, No. 1, Kent Korgenski et al.
2) Journal of Clinical Microbiology, April 2000, pages 1688-1693, Volume 38, No. 4.
3) Clinical Microbiology and Infection, Volume 10, No. 5-2004 Kolbert et al.
4) Journal of Clinical Microbiology, April 2005, pages 1846-1850, Volume 43, No. 4—Bert et al.
5) Journal of Microbiological Methods, 2008, Volume 75, pages 177-181.
6) International Journal of Antimicrobial Agents, 45 (215) 61-65—Lepage et al.

The invention claimed is:

1. A method of automatically analyzing and interpreting an antibiogram of a sample of a microorganism for analysis, the method serving to determine a phenotype of resistance or sensitivity to at least one antimicrobial compound, said phenotype being selected from a plurality of different reference phenotypes for each of the reference species of microorganism in a plurality of different species of reference microorganisms, wherein:
   a) the antibiogram of the sample is prepared using a methodology on a solid culture medium, which methodology comprises:
   depositing a concentration of microorganism of the sample of microorganism, on said solid culture medium;
   depositing a number n of a plurality of substrates on said solid culture medium, the substrates containing a concentration of antimicrobial compound(s) and suitable for diffusing one or more different antimicrobial compounds for each of the n substrates;
   incubating the sample of microorganism deposited on said solid culture medium under conditions and for a duration;
   b) acquiring a photographic image of the antibiogram of the sample obtained in step a); and
   c) determining said phenotype of the sample of microorganism, by using software to compare the photographic image obtained in step b) with reference images of reference antibiograms in a database,
   wherein said database comprises a plurality of at least p different reference images of antibiograms of p different strains of the same microorganism for each reference phenotype of each reference species of microorganism.

2. The method according to claim 1, further comprising preparing all of the reference antibiograms in step c) using the same said methodology as the antibiogram of the sample, and taking said reference images and the image for analysis with the same photographic image capture apparatus and under the same conditions comprising a same distance, a same brightness, a same background, and a same resolution.

3. The method according to claim 1, wherein a plurality, n, of said substrates is used, where n lies in the range 5 to 20, and said database comprises a plurality of at least p different reference images of antibiograms of p different strains of the same microorganism, where p is not less than 5.

4. The method according to claim 3, wherein n lies in the range 6 to 16, and wherein p is not less than 10.

5. The method according to claim 1, wherein, in step c), said software is used to compare the shape of the outline of the rings corresponding to inhibition zones around the substrates.

6. The method according to claim 5, wherein said substrates are in the form of wafers, and said software recognizes at least one of antibiotic code letters and dosage numerals specified on the wafers.

7. The method according to claim 1, wherein said microorganism is a bacterium, wherein a minimum acceptable similarity percentage between an image and a reference image is determined, referred to here as a similarity threshold, and wherein the bacterium of the sample is determined as presenting said reference phenotype of said reference bacterium if the recognition software evaluates a similarity percentage between the image of the antibiogram of the sample and a reference image corresponding to said reference phenotype of said reference species of bacterium that is not less than a minimum acceptable threshold similarity percentage.

8. The method according to claim 7, wherein the minimum acceptable threshold similarity percentage is at least 70%.

9. The method according to claim 1, wherein said microorganism is a bacterium, wherein a minimum threshold similarity percentage between said different reference images of different antibiograms of p different strains for each reference phenotype of each reference species of bacterium is determined, referred to here as the reference similarity threshold, wherein said reference similarity threshold percentage corresponding to the lowest similarity percentage between the two most different reference images for each reference phenotype of each reference species of bacteria is determined, and wherein the bacterium of the sample is determined as presenting said reference phenotype of said reference bacterium if the recognition software evaluates a similarity percentage that is not less than said reference similarity threshold between the image of the antibiogram of the sample and a reference image corresponding to said reference phenotype of said reference species of bacterium.

10. The method according to claim 1, wherein said reference phenotype is a resistance or sensitivity classification for a given antibiotic or group of antibiotics.

11. The method according to claim 10, wherein said reference phenotype includes a synergy phenotype between two antibiotics corresponding to two antibiotics for which the reference microorganism is resistant when they are taken separately and for which the reference microorganism is sensitive when they are taken in association.

12. The method according to claim 1, wherein the reference phenotype is a resistance or sensitivity classification for a plurality of antibiotics and/or for a group of antibiotics.

13. The method according to claim 1, wherein said reference species of microorganism is selected from the group consisting of *Escherichia coli, Klebsiella pneumoniae, Proteus mirabilis, Klebsiella oxytoca, Enterobacter cloacea, Enterobacter aerogenes, Entercoccus faecalis, Pseudomonas aeruginosa, Staphylococcus aureus,* and *Staphylococcus epidermidis.*

14. The method according to claim 1, wherein the antibiogram of the sample is made using wafers comprising the following antibiotics and with the following marking corresponding to said antibiotics: AMX for amoxicillin; AMC for amoxicillin-clavulanic acid; GEN for gentamicin; SXT for trimethoprim-sulfamethoxazole (cotrimoxazole); TIC for ticarcillin; TCC for ticarcillin-clavulanic acid; TZP for piperacillin-tazobactam; CAZ for ceftazidime; IMP for imipenem; COL or CL for colistin; FOX for cefoxitine; VAN or VA for vancomycin; TEC for teicoplanin; CLI or DA for clindamycin; CRO for ceftriaxone; FEP for cefepime; L or LIN for lincomycin; FUR or NT for nitrofurantoin; CIP for ciprofloxacin; OFX for ofloxacin; CTX for cefotaxime; AK or AN for amikacin; TOB or TM for tobramycin; FOX for cefoxitine; ATM for aztreonam; ERT for ertapenem; FF or FOS for fosfomycin; DOI for doxycycline; K for kanamycin; L or LIN for lincomycin; LNZ for linezolid; NA for nalidixic acid; NOR for norfloxacin; MET for metronidazole; MEM for meropenem; PT for pristinamycin; P for penicillin G; RA for rifampicin; TGC for tigecycline; TEL for telithromycin; E for erythromycin; and OX or OXA for oxacillin.

15. The method according to claim 14, wherein the antibiogram under analysis and/or said database comprises the reference phenotypes for the reference species of bacteria corresponding to the following inhibitors/resistances (I/R) or sensitivities (S) relative to concentrations of six antibiotic compounds selected from the following groups a1) to a6), arranged in a circle in the following order for each group:
   a1) AMX, AMC, TCC, CRO, FEP, and IMP,
   a2) AMX, AMC, TZP, CRO, FEP, and IMP,
   a3) AMC, TZP, CRO, FEP, IMP, and COL,
   a4) AMX, GEN, LIN, FUR, VAN, and TEC,
   a5) TIC, TCC, TZP, FEP, CAZ, and IMP, and
   a6) FOX, CLI, SXT, GEN, VAN, and TEC.

16. The method according to claim 14, wherein the antibiogram under analysis and/or said database comprises the following reference phenotypes for the following reference species of bacteria corresponding to the following inhibitors/resistances (I/R) or sensitivities (S) with respect to sixteen antibiotic compounds selected from the following groups b1) and b2), having their wafers arranged in a rectangular grid in the following order starting from the first row on the right with four rows of four compounds aligned in columns for each group:
   b1) CIP, OFX, TIC, COL, IMP, CTX, TCC, AK, SXT, AMC, CRO, TOB, AMX, ATM, FOX, and GEN, and
   b2) SXT, DA, FOX, OXA, PT, GEN, CIP, RA, TEC, VAN, LNZ, TOB, E, DO, and NT.

17. The method according to claim 1, wherein the reference phenotype is a resistance classification or selected from among at least the following phenotypes:
   phenotype "wild",
   phenotype "low level penicillinase",
   phenotype referred to as "penicillinase resistant to inhibitors",
   phenotype "high level penicillinase",
   phenotype "broad spectrum beta-lactamase" (BSBL),
   phenotype "high level cephalosporinase",
   phenotype "carbapenemase",
   phenotype "selective permeability to imipenem",
   phenotype "resistance to methicillin",
   phenotype "resistance to fluoroquinolones",
   phenotype "resistance to aminosides",
   phenotype "resistance to macrolides",
   phenotype "resistance to cotrimoxazole",
   phenotype "resistance to rifampicin", and
   phenotype known as "atypical phenotype".

18. The method according to claim 1, wherein, in step a), the reference antibiograms and the antibiogram of the sample are prepared on a solid culture medium of Mueller-Hinton agar type;

wherein the substrates are in a form of wafers;
wherein from six to sixteen wafers in the form of disks and having antibiotic concentrations in the range 10 μg to 300 μg are arranged in a circle or a rectangular grid;
wherein a bacterial concentration (CFU/mL) of the sample for analysis or of the reference deposited on said solid culture medium corresponds to a deposited suspension having opacity matching the 0.5 standard in the McFarland range; and
wherein the incubating step is carried out at 37° C. for 18 h to 24 h.

19. The method according to claim 1, wherein said microorganism is a bacterium, and said substrates are in the form of wafers.

20. The method according to claim 1, wherein incubating the sample of microorganism is carried out for a duration of 18 h to 24 h at a temperature in a range of 35° C. to 37° C.

21. The method according to claim 1, wherein acquiring a photographic image is carried out using a scanner or camera.

* * * * *